United States Patent
Dong et al.

(10) Patent No.: US 10,456,012 B2
(45) Date of Patent: Oct. 29, 2019

(54) DISPOSABLE ENDOSCOPE AND SYSTEM

(71) Applicant: Tao Dong, Shenzhen (CN)

(72) Inventors: Tao Dong, Shenzen (CN); Yongde Cai, Shenzhen (CN); Weiguo Xu, Shenzhen (CN); Kailiang Zhang, Shenzhen (CN); Rui Wang, Shenzhen (CN); Hong Guo, Shenzhen (CN); Cheng Chen, Shenzhen (CN)

(73) Assignee: Tao Dong, Shenzhen, Guangdong (CN)

( * ) Notice: Subject to any disclaimer, the term of this patent is extended or adjusted under 35 U.S.C. 154(b) by 355 days.

(21) Appl. No.: 15/508,780

(22) PCT Filed: Sep. 29, 2014

(86) PCT No.: PCT/CN2014/087775
§ 371 (c)(1),
(2) Date: Mar. 3, 2017

(87) PCT Pub. No.: WO2016/049804
PCT Pub. Date: Apr. 7, 2016

(65) Prior Publication Data
US 2017/0273545 A1    Sep. 28, 2017

(51) Int. Cl.
*A61B 1/005* (2006.01)
*A61B 1/00* (2006.01)
(Continued)

(52) U.S. Cl.
CPC .......... *A61B 1/00103* (2013.01); *A61B 1/008* (2013.01); *A61B 1/00009* (2013.01);
(Continued)

(58) Field of Classification Search
CPC ............ A61B 1/00105; A61B 1/00121; A61B 1/00128; A61B 1/0057; A61B 1/0055;
(Continued)

(56) References Cited

U.S. PATENT DOCUMENTS

| | | | | |
|---|---|---|---|---|
| 4,919,112 A | * | 4/1990 | Siegmund | A61B 1/00105 600/136 |
| 8,696,552 B2 | * | 4/2014 | Whitman | A61B 1/00135 600/133 |

(Continued)

FOREIGN PATENT DOCUMENTS

| | | |
|---|---|---|
| CN | 102319089 A | 1/2012 |
| CN | 102341057 A | 2/2012 |

(Continued)

OTHER PUBLICATIONS

International Search Report for PCT/CN2014/087775 dated Jun. 16, 2015 and its English translation provided by WIPO.

(Continued)

*Primary Examiner* — John P Leubecker
(74) *Attorney, Agent, or Firm* — Ladas & Parry, LLP (57) ABSTRACT

A disposable endoscope and system, the endoscope comprising: a tubular component, a linear drive piece controlling the component to bend, an image pickup unit at the front end of the component and a wiring harness connected thereto, a cladding layer wrapping around the integral structure, and a connector head and a disposable fixing piece both at one end of the piece away from the component. A first connector fixed at the head at one end of the piece is detachably engaged with a corresponding second connector of an external control base; the first connector is fixed by the disposable fixing piece with respect to the head, and can be moved in a length direction within a through hole of the head after the piece is removed.

15 Claims, 10 Drawing Sheets

(51) Int. Cl.
*A61B 1/008* (2006.01)
*A61B 1/05* (2006.01)
*G02B 23/24* (2006.01)

(52) U.S. Cl.
CPC ...... *A61B 1/00018* (2013.01); *A61B 1/00029* (2013.01); *A61B 1/0055* (2013.01); *A61B 1/0057* (2013.01); *A61B 1/00105* (2013.01); *A61B 1/00114* (2013.01); *A61B 1/00121* (2013.01); *A61B 1/05* (2013.01); *G02B 23/2476* (2013.01); *A61B 1/00066* (2013.01)

(58) Field of Classification Search
CPC .............. A61B 1/0052; A61B 1/00018; A61B 1/00066; G02B 23/2476
USPC ......................................... 600/136, 148, 149
See application file for complete search history.

(56) References Cited

U.S. PATENT DOCUMENTS

| | | | | | |
|---|---|---|---|---|---|
| 8,702,594 | B2* | 4/2014 | Edidin | ............... | H01R 13/6205 439/38 |
| 8,753,263 | B2* | 6/2014 | Arai | ..................... | A61B 1/0052 600/144 |
| 8,888,688 | B2* | 11/2014 | Julian | .................. | A61B 1/0053 600/146 |
| 2007/0129604 | A1* | 6/2007 | Hatcher | ............. | A61B 1/00048 600/136 |
| 2010/0191053 | A1* | 7/2010 | Garcia | ............... | A61B 1/00105 600/109 |
| 2015/0112142 | A1* | 4/2015 | Ando | ................. | A61B 1/00128 600/149 |
| 2015/0112143 | A1* | 4/2015 | Ando | .................. | A61B 1/0057 600/149 |

FOREIGN PATENT DOCUMENTS

| | | | |
|---|---|---|---|
| CN | 103417177 | A | 12/2013 |
| CN | 103533880 | A | 1/2014 |
| CN | 103917148 | A | 7/2014 |
| EP | 2604175 | A1 | 6/2013 |
| JP | 0625404 7 | A | 9/1994 |
| WO | WO-9315648 | A1 * | 8/1993 ......... A61B 1/00052 |
| WO | 2008086497 | A1 | 7/2008 |

OTHER PUBLICATIONS

Written Opinion of the International Search Authority for PCT/CN2014/087775 dated Jun. 16, 2015 and its English translation provided by WIPO.
From CN201480009341.3, Search Report, dated Jun. 20, 2016, with an English translation from Bing.com Microsoft Translator.
Written Opinion of the International Search Authority for PCT/CN2014/087775 dated Jun. 16, 2015 and its English translation provided WIPO.
International Preliminary Report on Patentability (IPRP; CH 1) for PCT/CN2014/087775 dated Apr. 13, 2017 and its English translation provided by WIPO.

* cited by examiner

(radial)   (axial)

DISPOSABLE ENDOSCOPE AND SYSTEM

CROSS-REFERENCE TO RELATED APPLICATIONS

The present application is the U.S. national phase of PCT Application PCT/CN2014/087775 filed on Sep. 29, 2014 entitled "DISPOSABLE ENDOSCOPE AND SYSTEM", the disclosure of which is hereby incorporated by reference.

TECHNICAL FIELD

The present disclosure relates to medical devices, specifically to medical endoscopes.

BACKGROUND

Figure 1:
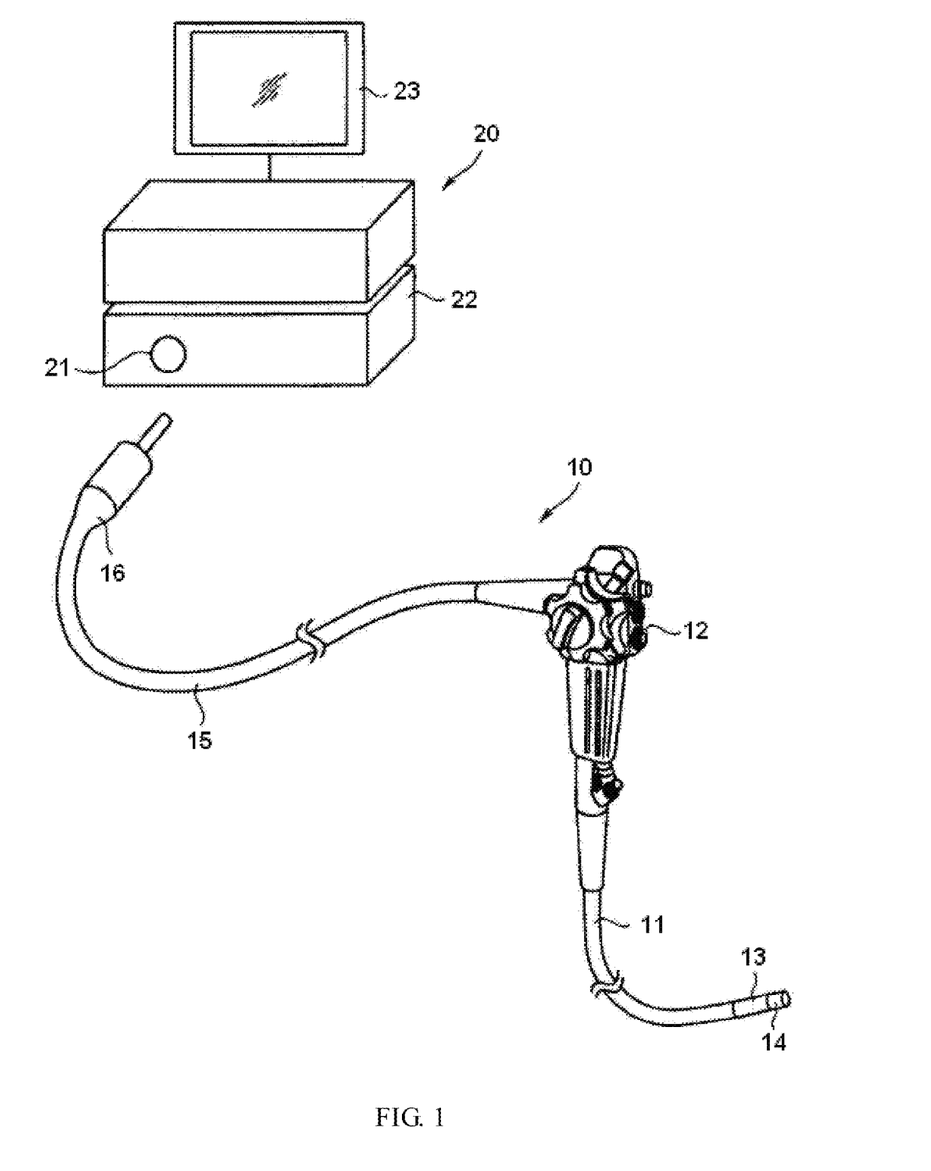
FIG. 1 is a schematic view of an existing endoscope system.

Endoscope systems are necessary equipments for diagnosis and treatment of diseases in modern medicine. Existing endoscope systems generally include an endoscope part and a host part, such as the endoscope systems described in the Chinese application with a publication number of CN103917148A. Referring to FIG. 1, the endoscope part generally includes a part 11 which will be inserted into a body cavity, and a mechanical control part 12. The part inserted into the body cavity mainly includes a tubular multi joint mechanical arm 13 (whose specific configuration is not shown in the figures and may be understood referring to the Chinese application with a publication number of CN102341057A, etc) and a camera 14 mounted on the front end of the mechanical arm. Transmission wires (usually four, and not shown in the figures) are inserted into the multi joint mechanical arm. One end of the transmission wires is fixed near the joint, and the other end is connected with the mechanical control part. An operator can control the bending of the multi joint mechanical arm by manipulating the mechanical control part to move the transmission wires in the length direction, such that the camera is able to shoot the region of interesting within the body cavity to obtain videos. The part inserted into the body cavity of the existing endoscope is clad by several layers made from a variety of materials (the specific configuration is not shown in the figures). For example, an inner layer may be a hose made from twisted metal wires, outside of which is clad by polyurethane materials, etc. The video data collected by the camera is transmitted through a dedicated data line 15 which is extended from the mechanical control part and connected to a data interface 21 of the host part 20 through a dedicated data connector 16. The host part generally includes a data processing system 22 and a display 23, etc, for processing and displaying the collected image data.

The existing medical endoscope is reusable and expensive. The selling price of one endoscope is up to about 300,000 Chinese yuan. Since it needs to be reused, after being used, each endoscope must undergo a strict and complicated sterilization procedure to avoid cross infection between patients. According to the related sterilization criteria issued by the Ministry of Health, an used endoscope should undergo a cleaning and sterilization process of 6-10 steps which take at least 20 minutes.

The current situation of the medical endoscope industry is that, on the one hand, the endoscope is expensive and the great acquisition cost leads to that the number of equipped endoscopes is greatly limited; on the other hand, the hospital needs to set up a dedicated sterilization chamber and equip it with dedicated sterilization equipments and corresponding operators, which further increases the operating cost of the endoscope, while the required sterilization procedure limits the frequency of reuse, which leads to that the patients need to pay not only the economic cost but also the time cost, and still take the risk of cross infection etc. caused by an imperfect sterilization. Furthermore, the frequent cleaning and sterilization processes will produce large amounts of liquid chemical waste and aggravate the environmental pollution.

For a long time, such a development path has been formed in the medical endoscope field that: the endoscope is expensive, so it needs to be reused, which necessitates it to be sterilized strictly, accordingly, the erosion caused by the sterilization needs to be resisted to extend the service life, which requires better materials and more sophisticated technologies, causing the endoscope to become more expensive. This development path makes the development of the medical endoscope fall into a cycle of high cost and high consumption.

Although the endoscope has been developed from early fiber-optic endoscope to electronic endoscope which collects images based on photosensitive chip, the cycle is not broken yet. But in fact, with the rapid development of electronic technology, the price of the camera etc. as the core elements for image collection has already become very low. For example, the cost of a conventional 300,000 pixels color CMOS camera assembly is only about 10 Chinese yuan.

SUMMARY

According to one aspect of the present disclosure, a disposable endoscope is provided. The disposable endoscope may include: a tubular part including a plurality of joints; linear transmission parts which are inserted into the tubular part, where one end of the linear transmission part is fixed with respect to one of the joints and the other end is provided with a first connector, the movement of the linear transmission parts along the length direction can cause the tubular part to bend, and the first connectors are used to be detachably engaged with the corresponding connectors of an external control seat; a camera unit mounted on the front end of the tubular part; a wire harness, where one end of the wire harness is connected with the camera unit and the other end is used to be connected with external power supply and data processing device, and the wire harness is used to provide the camera unit with power and transmit image data collected; a cladding layer cladding the tubular part and the extending linear transmission parts and wire harness; a connection head arranged on the end of the linear transmission parts away from the tubular part, where the connection head is provided with through holes through which the first connectors pass; and a disposable fastener, where the disposable fastener is used to fix the first connectors with respect to the connection head, and after the disposable fastener is removed the first connectors are able to be moved in the through holes of the connection head along the length direction.

According to another aspect of the present disclosure, a disposable endoscope system is provided. The disposable endoscope system includes the disposable endoscope described above and a control seat which is used to be connected with the disposable endoscope. The control seat includes: the second connectors which are used to be detachably engaged with the first connectors; a conductive interface which is used to be electrically connected with the other end of the wire harness; a connection seat which is provided with through holes through which the second connectors pass, where when the first connectors are engaged with the second connectors the through holes of the connection seat are aligned with the through holes of the connection head; a driving mechanism which is connected with the second connectors and used to control the movement of the second connectors along the length direction; and a limiting switch which is used to fix or release the second connectors with respect to the connection seat.

The disposable endoscope according to the present disclosure separates the driving parts and the image collection parts which need to be inserted into the body cavity. The linear transmission parts are connected with the driving mechanism by the cooperation of the connection head and the connection seat. Therefore, based on the situation that currently the electronic technology is mature, making the expensive device to be disposable is achieved. The advantages are not only that the complicated cleaning and sterilization processes are entirely omitted and the economic cost for the use of the endoscope is reduced, but also that the time cost for the use of the endoscope is also effectively reduced since the disposable endoscope can be provided in large quantity. The present disclosure will subvert the current industrial model of the endoscope industry and open up new directions for the development of the medical endoscope.

The embodiments of the present disclosure will be described in details in following with reference to the drawings.

DETAILED DESCRIPTION

The First Embodiment

Figure 2:
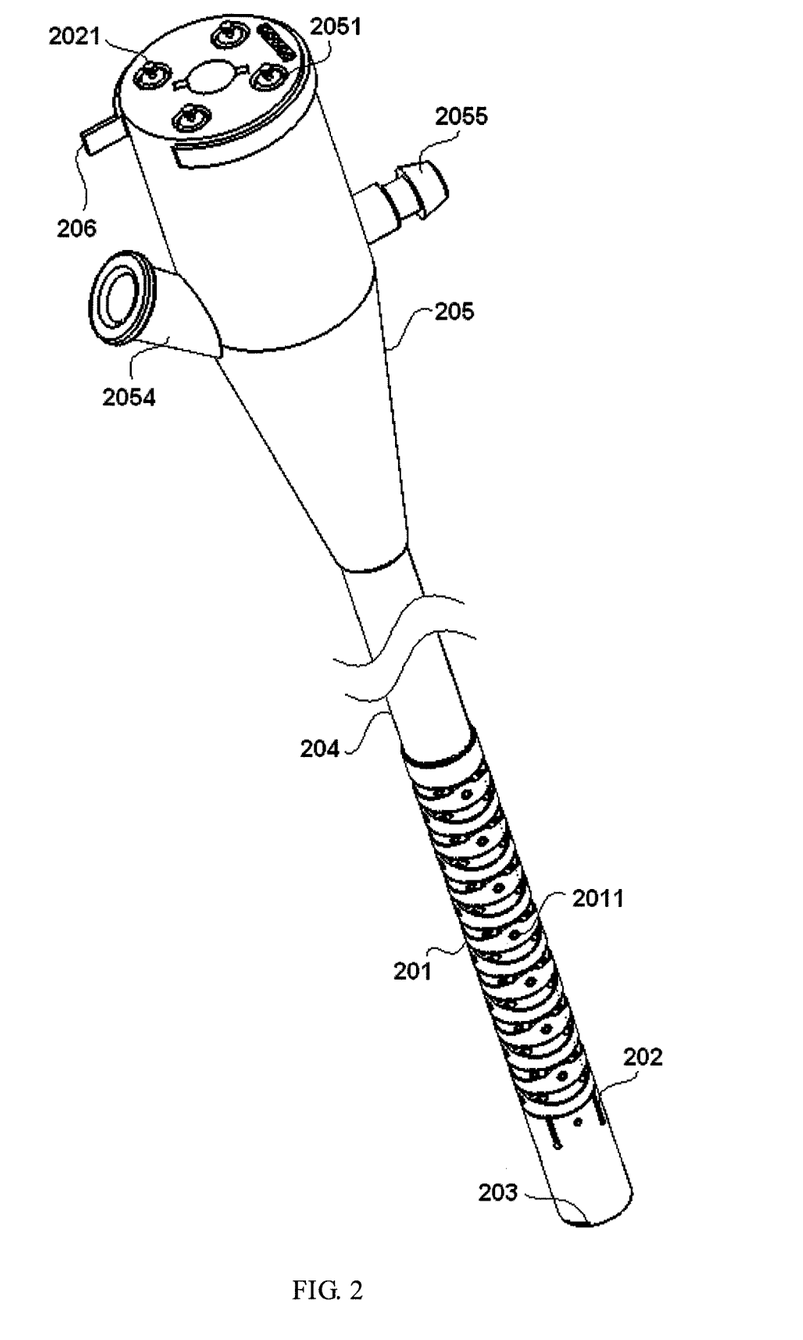
FIG. 2 is a schematic view of a disposable endoscope according to the first embodiment.
Figure 3:
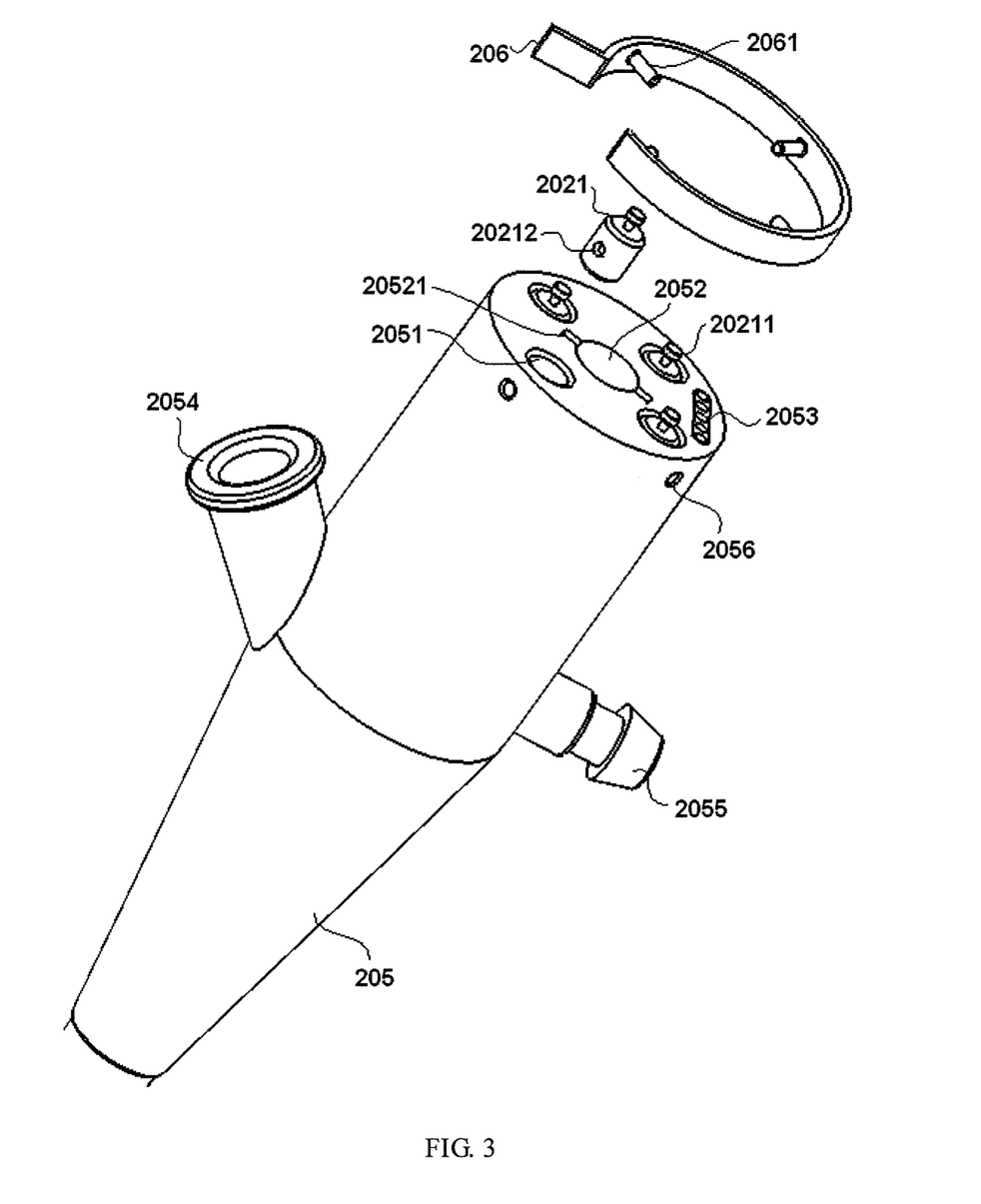
FIG. 3 is a schematic view of a connection head in the first embodiment.
Figure 4:
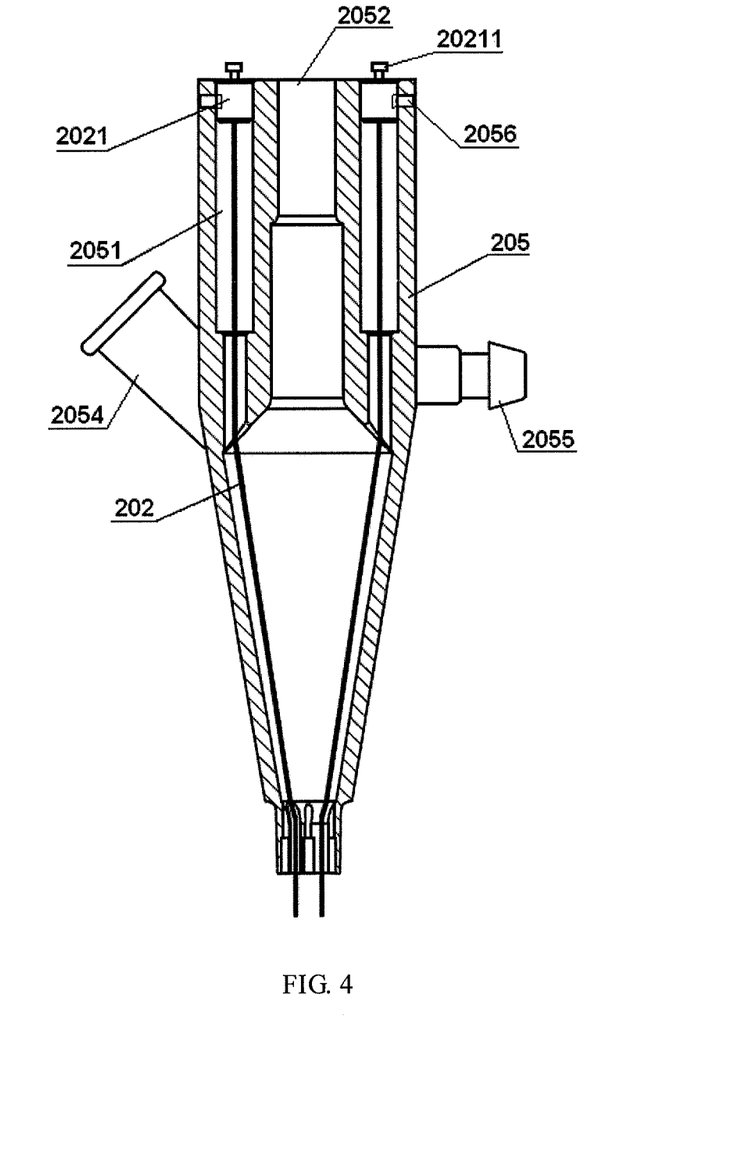
FIG. 4 is a schematic view showing a longitudinal section of the connection head in the first embodiment which passes through the through hole.

One embodiment of the disposable endoscope according to the present disclosure is shown in FIG. 2 to FIG. 4. The disposable endoscope may include a tubular part 201, linear transmission parts 202, a camera unit 203, a wire harness (not shown), a cladding layer (not shown entirely), a connection head 205 and a disposable fastener 206.

The tubular part 201 includes a plurality of joints 2011. The tubular part may employ a variety of structures which are able to achieve a controllable bending operation through linear transmission parts, which will not be limited by the present embodiment, and what is shown in the figures is merely an example. Furthermore, in order to show the tubular part, the cladding layer which clads the tubular part is not shown in FIG. 2. Because it does not need to be reused, the tubular part may be made from materials of plastic, etc. in order to reduce the cost. For example, the tubular part may be made by a simple processing technology such as injection molding.

The linear transmission parts 202 are inserted into the tubular part. One end of the linear transmission parts 202 is fixed with respect to one of the joints of the tubular part (for example, is fixed near the forefront joint), and the other end is provided with first connectors 2021. The movement of the linear transmission parts along the length direction can lead to the bending of the tubular part. The linear transmission parts may generally employ steel wires, or may also employ other kinds of materials whose strength and stretchability meet the requirements.

The camera unit 203 is mounted on the front end of the tubular part. The camera unit may employ a variety of structures which can achieve digital image collection. For example, the camera unit generally may include a lens, a photosensitive chip, a lighting unit and an integrated circuit board which provides corresponding control functions. Preferably, the lighting unit may employ brightness-adjustable LED cold light source. The camera unit may employ an existing universal small camera assembly (for example, the common camera assembly used in mobile phone), or may also employ a dedicated camera assembly made for the disposable endoscope (for example, may be designed as having a cylindrical shape corresponding to the diameter of the tubular part). A person skilled in the art will understand that, since the camera technology is a very mature technology, the use of the dedicated camera assembly will not greatly increase the cost. It should be noted that the camera unit and the tubular part are divided into two parts based on respective functions and the mechanical structural parts of them can be combined with each other. For example, the package of the camera unit can be integrated with the front end of the tubular part, or the package of the camera unit itself can be a part of the front end of the tubular part.

The wire harness is hidden inside of the structure and thus not shown. One end of the wire harness is connected with the camera unit, and the other end is connected with an external power supply and a data processing device (for example, a host) so as to provide the camera unit with power and transmit the image data collected. It is worth mentioning that the existing endoscope system usually uses dedicated power supply and data transmission method, which leads to that the circuit is complicated and a specially designed electrical connector is needed, thereby forming a technical barrier. However, based on the mature camera technology, a simpler circuit is possible. Therefore, as a preferred example, the wire harness of the disposable endoscope according to the present disclosure may employ a common electrical connection (for example, a electrical connection based on a common USB protocol) to perform the transmission of the power and the data, which can not only reduce the number of lines in the wire harness (typically 5), but also lead to a good versatility of the circuit interface between the endoscope and the host. Therefore, the difficulty of the development of the host system is effectively reduced, thereby reducing the overall cost of the endoscope system. There is reason to believe that it is possible to implement the host of the endoscope system by installing appropriate processing software in conventional computer hardware.

The cladding layer clads the tubular part, the extending linear transmission parts and the wire harness. It will be readily understood that, based on the different parts clad by the cladding layer, the cladding layer may include different sections which employ different materials and different package methods. For example, since the tubular part itself includes supportive structures and needs to be bended, it can be clad by a film (not shown). While because the wires extending out of the tubular part have no supportive structures, the section extending from the rear end of the tubular part to the connection head can employ a hose 204 with a certain thickness as the cladding layer. Since it does not need to be reused and the resistance against the erosion caused by the harsh sterilization conditions does not need to be considered, as a preferred example, the cladding layer of the variety of sections can all be single layer. This way, not only the packaging process is simple, but also the diameter of the endoscope can be effectively reduced, thereby reducing the pain suffered by the patients during the examination. Since there is no requirement for durability and corrosion resistance for the cladding layer, generally the materials with good biocompatibility can be used. For example, the film may employ a medical thermoplastic elastomer film (TPE/TPR), etc. and the hose may employ medical silicone, etc.

The connection head 205 is arranged at the end of the linear transmission parts away from the tubular part, and is provided with through holes 2051 through which the first connectors pass. Since it is disposable and relatively simple, the connection head may be made from plastic materials and manufactured by a simple process such as injection molding, etc.

The disposable fastener 206 is used to fix the first connectors with respect to the connection head. After the disposable fastener is removed, the first connectors can be moved in the through holes of the connection head along the length direction. The disposable fastener is mainly used to fix the first connectors before the connection head is connected to the connection seat to facilitate the connection operation. After the connection operation is completed, the disposable fastener can be removed.

In the present embodiment, as a preferred structure, the first connectors 2021 are cylindrical in shape. The cross-sectional sizes of the first connectors match the cross-sectional sizes of the through holes 2051 of the connection head. The ends of the first connectors are provided with male connectors 20211 which are used to detachably engage the corresponding connectors of an external control seat. Specifically, the mal connectors 20211 are used to snap with corresponding female connectors of the external control seat. It will be readily understood by a person skilled in the art that the first connectors are interchangeable with the connection structure of the corresponding connectors of the external control seat. For example, the recessed female connectors may be arranged in the first connectors while the protruded male connectors may be arranged on the external control seat.

It is worth mentioning that, since the first connectors are disposable parts while the external control seat is a permanent non-disposable part, it can be considered when designing the connection structures therebetween that the structures which are easy to manufacture or have low requirements for the materials are arranged at the first conneceters while those which are relatively difficult to manufacture or have high reliability requirements are arranged on the control seat.

The structures of the first connectors of the present embodiment are merely examples. It will be readily understood by a person skilled in the art that the engagement of the first connectors with the corresponding connectors may be achieved by a variety of detachable mechanical structures. For example, in an embodiment, the end of the first connector may be a ring while the corresponding connector is provided with a pliers-shaped end which is controllable to open and close. The engagement can be implemented by closing the pliers-shaped end to grip the ring of the end of the first connector, and the detachment can be implemented by opening the pliers-shaped end to release the ring of the end of the first connecter. In another example, the end of the first connector may employ the male connector according to the present embodiment, while the corresponding connector employs a gripping mechanism which is controllable to release and grip and the engagement can be implemented by gripping the neck of the male connector. It is obvious that a variety of achievable detachable engagements can be designed based on the existing knowledge of mechanics. Therefore, the specific structure of the first connector will not be interpreted as limitations to the present disclosure. Furthermore, the relative size of the first connector and the through hole of the connection head are related to the specific implementation of the connection and belong to design characteristics. In the present disclosure, the through hole of the connection head may serve as a position-limit mechanism which limits the first connector to move only along the length direction such that the displacement of the first connector can be better controlled. In other connections, for example in the case of the disposable fastener fixing the first connector in several dimensions, there may be great difference between the sizes of the first connector and the through hole of the connection head.

In the present embodiment, as a preferred structure, a limiting hole 2052 may be provided at the center of the end face of the connection head 205. The limiting hole 2052 may be used for snapping with a corresponding limiting pile on the external control seat. It will be readily understood that the positions of the limiting hole and the limiting pile are interchangeable. Since the connection head is disposable part, it is preferred that the limiting hole is arranged in the connection head for saving materials. This kind of structure connecting the center of the end face of the connection head with the center of the end face of the control seat can effectively increase the stability of the connection between the disposable endoscope and the permanent parts to ensure that the connections of the mechanical transmission parts can run smoothly. Similar to the first connector, the specific structures for the engagement of the limiting hole with the limiting pile can be designed based on the existing knowledge of mechanics. For example, a gripping structure using spring clips or a tight fit relying solely on the friction force between the materials can be used.

In the present embodiment, exemplarily, there are four first connectors 2021 and the through holes 2051 in the connection head 205 are arranged on a same circumference around the center of the end face of the connection head. Obviously, the number of the first connectors is determined by the number of the linear transmission parts. Therefore, based on the different mechanical transmission structures (the structures for matching the tubular part and the linear transmission part), the number of the first connectors may vary. The uniform arrangement of the through holes 2051 in the present embodiment can facilitate the connection operation and provide better operational stability.

In the present embodiment, as a preferred structure, conductive contacts 2053 may further be arranged on the end face of the connection head 205. Each of the conductive contacts is electrically connected with a line in the wire harness, respectively. When the first connectors engage with the corresponding connectors of the external control seat, the conductive contacts are electrically connected with corresponding conductive interfaces of the control seat, thereby introducing external power supply and data processing devices through the lines of the control seat. This preferred structure achieves the connections of both the mechanical transmission and the electrical signal in a single connection operation of the connection head, and thus increases the convenience of using the disposable endoscope. In other embodiments, the structures similar to the existing endoscope may be used, i.e., the wire harness is extended out through a dedicated opening in the connection head and directly connected with a host which provides power supply and data processing functions.

In the present embodiment, as a preferred structure, the connection head 205 may further be provided with a biopsy entrance 2054 and a gas and water entrance 2055. Correspondingly, the package of the camera unit may be provided with through holes (not shown) which communicate with the interior of the tubular part. Passages starting from the biopsy entrance and the gas and water entrance may pass through the connection head and extend to the corresponding through holes located in the forefront package through the hose and the interior of the tubular part. This preferred structure further increases the degree of functional integration of the connection head and enables the disposable endoscope to be used in conjunction with the medical devices such as biopsy forceps, air pump and water pump, etc. In other embodiments, either or both of the biopsy entrance and gas and water entrance may not be used as required.

In the present embodiment, as a preferred structure, the disposable fastener 206 may be an arcuated buckle, the shape of which matches the cross-sectional profile of the connection head 205. The inner wall of the arcuated buckle is provided with an inward protrusion 2061. The side wall of the connection head is provided with a positioning hole 2056 which extends to the through hole 2051. The side of the first connector is provided with a recessed hole 20212 which corresponds to the position of the positioning hole. The protrusion of the arcuated buckle passes through the positioning hole and snaps into the recessed hole on the side of the first connector to fix the first connector. In order to ensure the nature of disposability, the arcuated buckle may be made from brittle materials such that it will be broken when being removed from the connection head and thus can not be reused. Or, in other embodiments, the two ends of the arcuated buckle may be connected by a vulnerable part to form a closed ring. When used, the arcuated buckle may be released and removed from the connection head by removing the vulnerable part. It will be readily understood that the specific structures of the disposable fastener are not limited to the example above. Rather, when the design of the connection structure varied, a disposable fastening structure which matches the connection structure can also be designed based on the existing knowledge of mechanics.

The Second Embodiment

Figure 5:
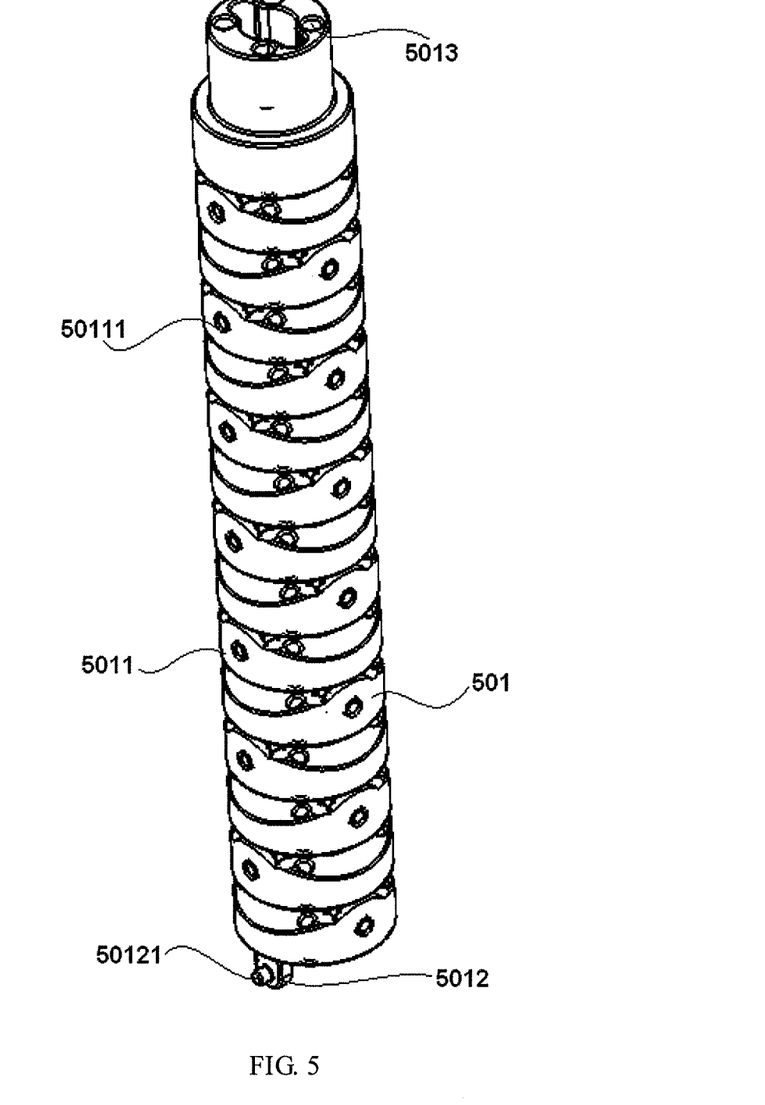
FIG. 5 is a schematic view of a tubular part in the second embodiment.
Figure 6:
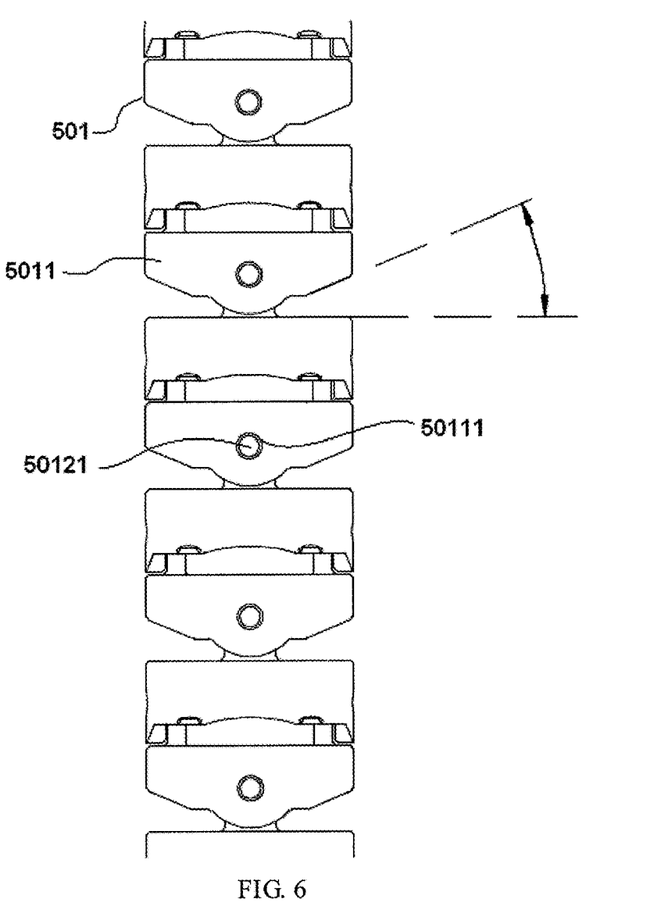
FIG. 6 is a radially projected schematic view of the tubular part in the second embodiment.
Figure 7:
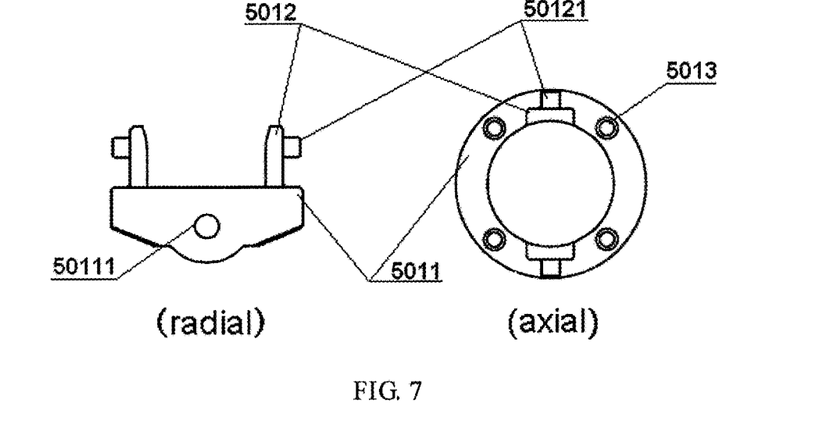
FIG. 7 shows the radially and axially projected schematic views of an annular unit of the tubular part in the second embodiment.

The present embodiment provides a preferred structure of the tubular part of the disposable endoscope according to the present disclosure. Referring to FIG. 5 to FIG. 7, the tubular part with this preferred structure includes a plurality of annular units 501. Each annular unit includes a cylindrical body 5011 and lugs which are located at both sides of the cylindrical body and extend along the axial direction. The cross sections of the cylindrical body are provided with through holes 5013 through which the linear transmission parts (not shown) pass. The ends of the lugs are provided with pins 50121 which are radially outwardly protruded, and the side wall of the cylindrical body is provided with connection holes 50111 which cooperate with the pins. The lugs and the connection holes in the same cylindrical body are crosswise arranged. One annular unit is connected to an adjacent annular unit by snapping its pins into the connection holes of the adjacent annular unit, and the junction forms the joint. The profile of the interconnected portions of the two adjacent annular units is wedge (show by dash lines in FIG. 6) and the vertex of the wedge is located at the joint. It will be readily understood that the annular units which are located at the head end and/or tail end may have different structures from those which are located at the middle so as to facilitate the connection of other parts. For example, the annular unit located at the tail end may be provided with an extending cylindrical tail part in order to facilitate the connection of the hose. For another example, the annular unit located at the head end may be integrated with the package of the camera unit installed. The annular unit located at the head end may not be provided with the lugs, but merely include the connection hole which will be connected by subsequent annular unit. The "a plurality of annular units" mentioned above may be understood as the group of the annular units of the tubular which are located the middle and have the same structure, except those located at the head end and the tail end.

The preferred structure of the tubular part mentioned above have many advantages. On the one hand, the annular unit may be made from plastic materials with a certain elasticity and manufactured by injection molding, and the connection of two adjacent annular units can be achieved by pressing the lugs of one of the two annular units by one hand (to reduce the distance between the lugs), pressing the cylindrical body of the other of the two annular units by the other hand (to increase the distance between the connection holes), snapping the pins of the lugs into the connection holes of the cylindrical body, and removing the pressing force to let the annular units restore, therefore the assembly of the tubular part can be done by hand without the use of any tools and the assembly process is simple; on the other hand, the wedge-shaped back angle between two adjacent annular units which is formed by the shape of the annular units enables each of the joints to have greater activity space, which facilitates the tubular part to achieve greater bending angle such that the disposable endoscope have more flexible observation range.

The Third Embodiment

Figure 8:
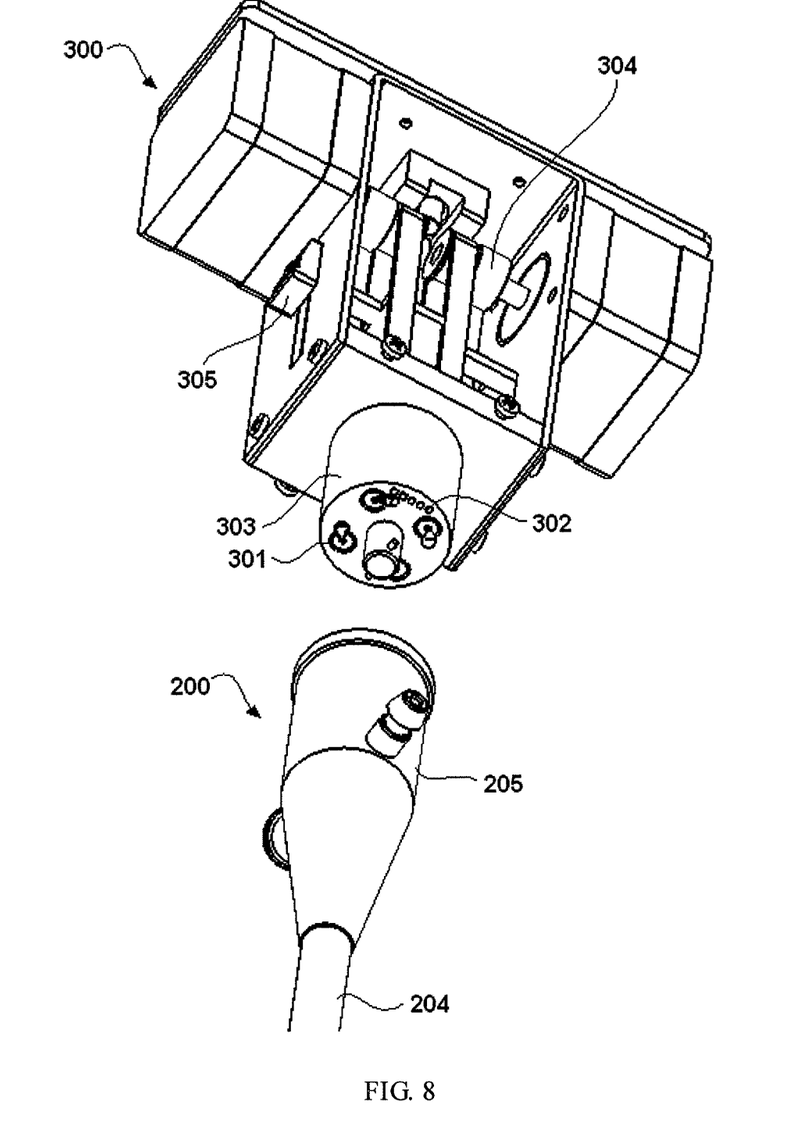
FIG. 8 is a schematic view of a disposable endoscope system according to the third embodiment.

One embodiment of the disposable endoscope system according to the present disclosure is shown in FIG. 8, which includes a disposable endoscope 200 and a control seat 300. The disposable endoscope 200 may employ the structures described in the first embodiment. The structures of the control seat 300 are described in FIG. 8 to FIG. 11, which includes second connectors 301, a conductive interface 302, a connection seat 303, a driving mechanism 304 and a limiting switch 305.

Figure 9:
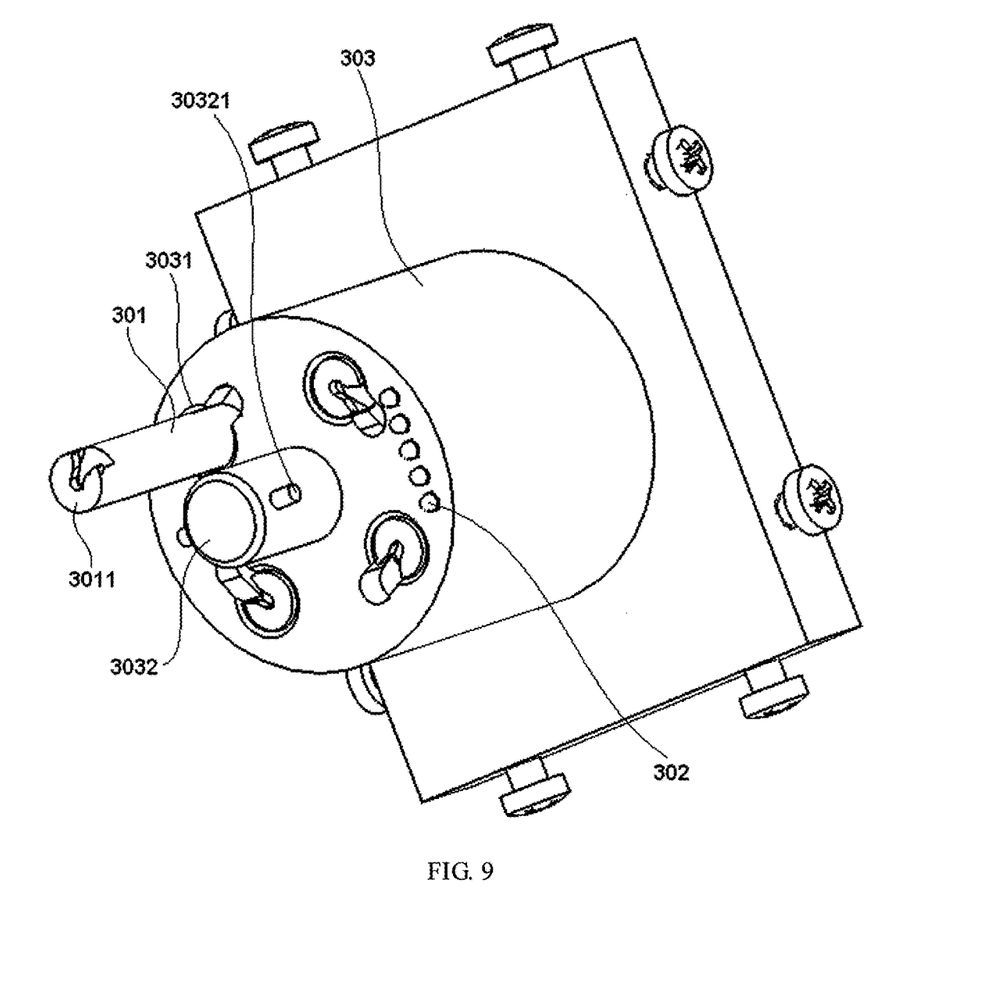
FIG. 9 is a schematic view of the connection seat in the third embodiment.
Figure 10:
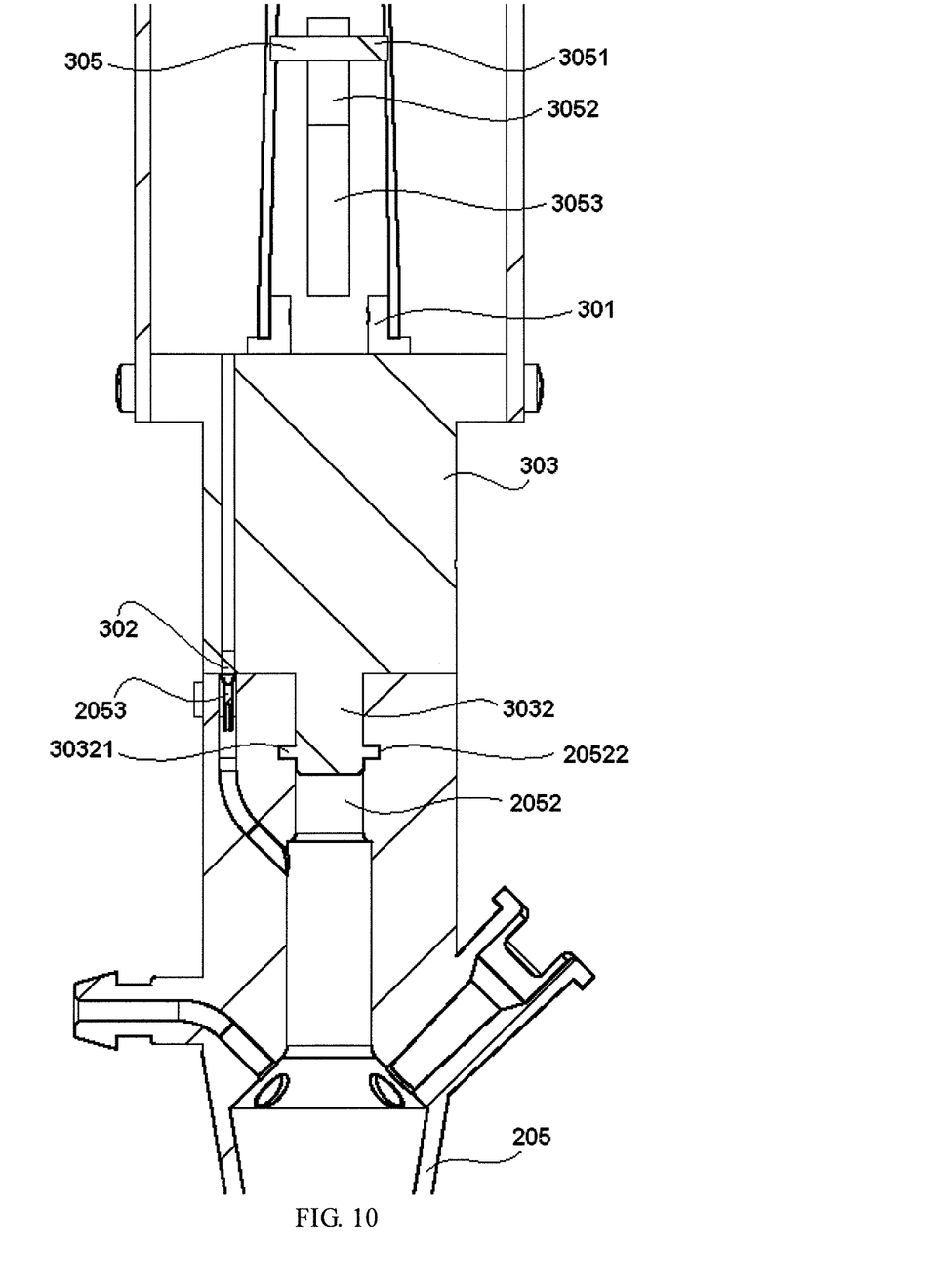
FIG. 10 is schematic view showing a longitudinal section of the interconnected portions of the connection head and the connection seat in the third embodiment which does not pass through the through hole.

The second connectors 301 detachably engage the first connectors. Based on the correspondence with the structures in the first embodiment, in the present embodiment, as a preferred structure, the second connectors are cylindrical in shape and the cross-sectional sizes of the second connectors are same with the cross-sectional sizes of the first connectors, and the end of the second connectors are provided with recessed female connectors 3011 which correspond to the first connectors. The side of the female connector is provided with an opening such that the corresponding male connector is able to be rotated into the female connector through the opening to achieve the snap engagement. Similarly corresponding to the first connectors, there are four second connectors which are arranged on a same circumference around the center of the end face of the connection seat.

The conductive interface 302 is used to be electrically connected with the wire harness of the disposable endoscope. Since the wire harness in the first embodiment is conducted through the conductive contacts 2053 arranged on the end face of the connection head 205, in the present embodiment, as a preferred structure, the conductive interface 302 is arranged on the end face of the connection seat 303, and the location of the conductive interface is designed in such a way that when the first connectors engage the second connectors the conductive contacts are able to contact with the conductive interface to achieve the electrical connection. Particularly preferably, when the wire harness of the disposable endoscope employs USB-based transmission, the conductive interface 302 may have 5 contacts (which specifically may be, for example, spring contacts slightly protruding out of the end face) to increase the reliability of the connection with the conductive contacts of the connection head of the endoscope.

The connection seat 303 is provided with through holes 3031 through which the second connectors 301 pass. Similar to the fit relationship between the first connectors and the through holes of the connection head, the size of the cross sections of the through holes of the connection seat matches the size of the cross sections of the second connectors. When the first connector engages the second connector, the through hole 3031 of the connection seat is aligned with the through hole 2051 of the connection head such that after the engagement of the two connectors, the two connectors can be moved in the connected through holes to smoothly transfer the driving force to the linear transmission parts. Based on the correspondence with the structure in the first embodiment, in the present embodiment, as a preferred structure, the center of the end face of the connection seat may be further provided with a limiting pile 3032 which corresponds to the center of the end face of the connection head. The limiting pile is used to be engaged with the limiting hole 2052. As an exemplary structure, the limiting pile is provided with locking protrusions 30321 which are extended along the radial direction, and the inner wall of the limiting hole is provided with axial slides 20521 (see FIG. 3) which cooperate with the locking protrusion and a circumferential slide 20522 which is located at a depth corresponding to the axial location of the locking protrusion such that the limiting pile can snap with the limiting hole by rotation after being inserted into the limiting hole. The rotation of the limiting pile and the limiting hole is synchronous with the rotation of the male connectors into the female connectors.

The driving mechanism 304 is connected with the second connectors and used to control the movement of the second connectors along the length direction. It will be readily understood that the driving mechanism can employ a variety of appropriate mechanical or electrical driving modes and the driving mode and the specific structures of the driving mechanism are not limited by the present embodiment. For example, the structure that a pulley is driven by a stepper motor and a belt driven by the pulley is fixed at the tail end of the second connector may be used.

Figure 11:
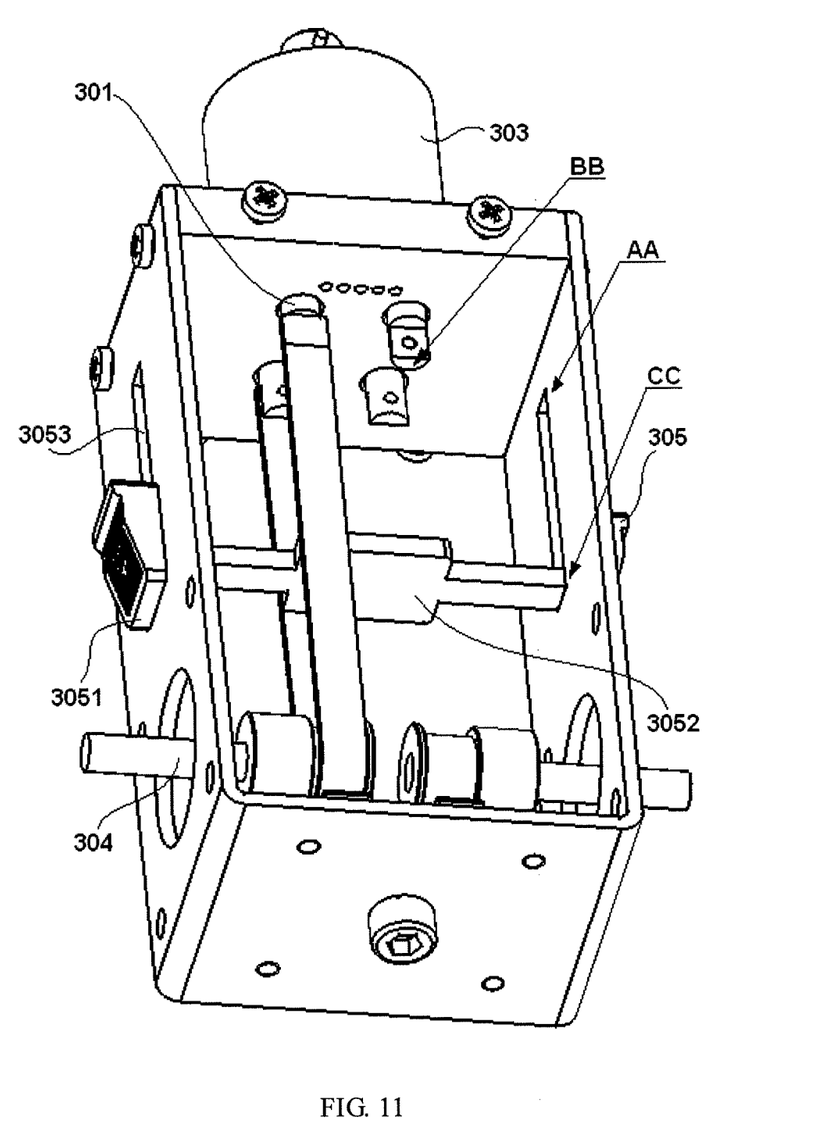
FIG. 11 is a schematic view of a limiting switch in the third embodiment.

The limiting switch 305 is used to fix or release the second connectors with respect to the connection seat. Before performing the connection operation, the function of the limiting switch is similar to the disposable fastener, which is fixing the second connectors so as to facilitate the performance of the connection operation. After the connection operation is completed, the limiting switch needs to release the second connectors such that they can move along the through hole. The difference from the disposable fastener is that, after the disposable endoscope is used, the limiting switch needs to fix the second connectors again so as to facilitate the remove of the connection. Therefore, the limiting switch can be understood as a mechanical structure with two work states which can be alternately switched, and the specific structures of it thus can be accordingly designed by the person skilled in the art.

In the present embodiment, as a preferred structure, the limiting switch 305 is arranged on the back side of the connection seat 303 and includes a slider 3051 and a limiting plate 3052. The slider is arranged in the slide 3053 which is extended along the movement direction of the second connector and can move along the slide between a locking position and a releasing position. The length of the slide is greater than the maximum travel of the second connector (for example, generally 2 to 3 centimeters). The limiting plate is fixedly connected with the slider. When the slider is positioned at the locking position AA, the limiting plate abuts against the rear end face BB of the second connector and limits the second connector in the through hole of the connection seat. When the slider is positioned at the releasing position CC, the second connector can move in the space in front of the limiting plate. Further preferably, in order to increase the reliability and the stability of the operation, the slider and the slide may be symmetrically arranged at both sides of the movement direction of the second connector and the limiting plate may be located between two sliders. Specifically, the slide may be arranged in a frame which forms the housing of the connection seat, and the shape of the slider may be designed as a shape which facilitates the push of the finger. It will be readily understood that, based on the preferred structure above, the length of the second connector is the same with the length of the through hole of the connection seat. Therefore, when the connection operation is to be performed, the limiting plate limits the second connector in the through hole of the connection seat and the female connector at the top of the second connector is just flush with the end face of the connection seat, while the male connector at the top of the first connector fixed by the disposable fastener is also just protruded out of the end face of the connection head, which enable the interconnection of the two connectors.

For better understanding of the embodiments above, the working process of the disposable endoscope system based on the third embodiment will be described briefly in following.

1. Preparation: confirming that the disposable fastener 206 of the disposable endoscope 200 is intact, and confirming that the limiting switch 305 of the control seat 300 is positioned at the locking position.

2. Connection: aligning the limiting hole 2052 in the connection head of the disposable endoscope with the limiting pile 3032 on the connection seat. Specifically, the locking protrusions 30321 is aligned with and then inserted into the axial slides 20521. When the end faces of the connection head and the connection seat contact with each other, the male connector 20211 of the first connector is inserted into the opening at the side of the female connector 3011 of the second connector. Then the connection head is rotated along the direction of entering the opening (in order to facilitate the operation of the user, an arrow identifying the direction may be marked on the body of the connection seat) such that the male connector is snapped with the female connector and simultaneously the limiting hole is snapped with the limiting pile. At this time, the through hole of the connection head is aligned with the through hole of the connection seat, and the conductive contacts 2053 on the end face of the connection head are electrically connected with the conductive interface 302 on the end face of the connection seat.

3. Usage: removing the disposable fastener after the connection is completed and pushing the limiting switch to the releasing position. Then the location and angle of the camera unit 203 can be controlled by controlling the driving mechanism 304 (for example, by manipulating the buttons on the control panel of the driving mechanism or manipulating a remote control) to obtain the image data collected by the camera unit.

4. Remove: restoring the limiting switch to the locking position after the usage is completed (it may be achieved by directly pushing the second connector back into the through hole using the limiting switch to synchronously complete the restoration and limiting operations, or by controlling the driving mechanism to restore the second connector first, and then limiting the second connector using the limiting switch), rotating the connection head in the direction opposite to its rotation direction when it is connected to the connection seat, and pulling out the connection head after the snap engagement is released. The removed disposable endoscope may be discarded and a new disposable endoscope may be used to repeat the processes above to continue to examine the patients without waiting.

The principle and embodiments of the present disclosure are described wither reference to the specific examples hereinabove. It should be understood that the embodiments above are merely used to facilitate understanding the present disclosure, but should not be interpreted as limitations to the present disclosure. For a person ordinarily skilled in the art, variations to the specific embodiments above may be made according to the concept of the present disclosure.

We claim:

1. A disposable endoscope comprising:
   a tubular part including a plurality of joints;
   linear transmission parts inserted into the tubular part, wherein one end of each linear transmission part is fixed with respect to one of the joints, the other end of each linear transmission part is provided with a respective one of first connectors, a movement of the linear transmission part along its length direction is able to cause the tubular part to bend, and each first connector is used to detachably engage with a corresponding connector of an external control seat;
   a camera unit mounted on a front end of the tubular part and connected with an external power supply and a data processing device to provide the camera unit with power and transmit image data collected;
   a cladding layer cladding the tubular part and the linear transmission parts;
   a connection head arranged at one end of the linear transmission parts away from the tubular part, wherein the connection head is provided with through holes through which the first connectors pass; and
   a disposable fastener which is used to fix the first connectors with respect to the connection head, wherein after the disposable fastener is removed, each first connector is able to be moved in a respective through hole of the connection head along their length direction.

2. The disposable endoscope of claim 1, wherein, each first connector is cylindrical in shape and cross-sectional size of each first connector matches cross-sectional size of each through hole of the connection head, an end of each first connector is provided with a protruded male connector or a recessed female connector which is used to snap with a corresponding female connector or male connector of the external control seat, and a side of the female connector is provided with an opening such that the corresponding male connector is able to be rotated into the female connector through the opening.

3. The disposable endoscope of claim 2, wherein a center of an end face of the connection head is provided with a limiting hole or a limiting pile which is used to snap with a corresponding limiting pile or limiting hole of the external control seat.

4. The disposable endoscope of claim 3, wherein there are four first connectors and the through holes in the connection head are arranged on a same circumference around the center of the end face of the connection head.

5. The disposable endoscope of claim 1, wherein, conductive contacts are arranged on the end face of the connection head, and when the first connectors engage with the corresponding connectors of the external control seat, the conductive contacts are electrically connected with a corresponding conductive interface of the control seat.

6. The disposable endoscope of claim 1, wherein, a package of the camera unit is provided with through holes which communicate with interior of the tubular part, the connection head is further provided with a biopsy entrance and/or a gas and water entrance, and a passage starting from the biopsy entrance and/or the gas and water entrance passes through the connection head and extends to the through hole in the package.

7. The disposable endoscope of claim 1, wherein, the tubular part includes a plurality of annular units, each annular unit includes a cylindrical body and lugs which are located at both sides of the cylindrical body and extend along an axial direction, cross sections of the cylindrical body are provided with through holes through which the linear transmission parts pass, an end of the lug is provided with a pin which is radially outwardly protruded, a side wall of the cylindrical body is provided with a connection hole which cooperates with the pin, the lugs and the connection holes in a same cylindrical body are crosswise arranged, one annular unit is connected to an adjacent annular unit by snapping its pins into the connection holes of the adjacent annular unit and the junction forms the joint, and a profile of the interconnected portions of the two adjacent annular units is a wedge a vertex of which is located at the joint.

8. The disposable endoscope of claim 1, wherein, the disposable fastener is an arcuated buckle the shape of which matches a cross-sectional profile of the connection head, an inner wall of the arcuated buckle is provided with an inward protrusion, a side wall of the connection head is provided with a positioning hole extending to the through hole, a side of each first connector is provided with a recessed hole which corresponds to position of the positioning hole, and the protrusion of the arcuated buckle passes through the positioning hole and snaps into the recessed hole on the side of each first connector to fix each first connector.

9. A disposable endoscope system comprising a disposable endoscope and a control seat,
wherein the disposable endoscope comprises:
a tubular part including a plurality of joints;
linear transmission parts inserted into the tubular part, wherein one end of each linear transmission part is fixed with respect to one of the joints, the other end of each linear transmission part is provided with a respective one of plural first connectors, and a movement of the linear transmission part along its length direction is able to cause the tubular part to bend;
a camera unit mounted on a front end of the tubular part and connected with an external power supply and a data processing device to provide the camera unit with power and transmit image data collected;
a cladding layer cladding the tubular part and the linear transmission parts;
a connection head arranged at one end of the linear transmission parts away from the tubular part, wherein the connection head is provided with through holes through which the first connectors pass; and
a disposable fastener which is used to fix the first connectors with respect to the connection head, wherein after the disposable fastener is removed, each first connector is able to be moved in a respective through hole of the connection head along its length direction;
wherein the control seat comprises:
second connectors which are used to detachably engage with the first connectors;
a conductive interface which is used to be electrically connected with the camera unit;
a connection seat which is provided with through holes through which the second connectors pass, wherein when the first connectors engage with the second connectors, the through holes of the connection seat are aligned with the through holes of the connection head;
a driving mechanism which is connected with the second connectors and used to control a movement of the second connectors along their length direction; and
a limiting switch which is used to fix or release the second connectors with respect to the connection seat.

10. The system of claim 9, wherein:
each first connector is cylindrical in shape and cross-sectional size of each first connector matches cross-sectional size of each through hole of the connection head, and an end of each first connector is provided with a protruded male connector or a recessed female connector;
each second connector is cylindrical in shape and cross-sectional size of each second connector matches the cross-sectional size of each through hole of the connection seat and is the same as the cross-sectional size of respective first connector, and an end of each second connector is provided with a recessed female connector or a protruded male connector which corresponds to each first connector; and
a side of the male connector is provided with an opening such that the corresponding male connector is able to be rotated into the female connector through the opening to achieve a snap engagement.

11. The system of claim 10, wherein,
a center of an end face of the connection head is further provided with a limiting hole or a limiting pile,
a center of an end face of the connection seat is further provided with a limiting pile or a limiting hole which corresponds to the center of the end face of the connection head; and
the limiting pile is able to be snapped with the limiting hole.

12. The system of claim 11, wherein,
the limiting pile is provided with a locking protrusion extending along a radial direction, and an inner wall of the limiting hole is provided with an axial slide which cooperates with the locking protrusion and a circumferential slide which is located at a depth corresponding to an axial location of the locking protrusion such that the limiting pile is able to snap with the limiting hole by rotating after being inserted into the limiting hole; and
the rotation of the limiting pile and the limiting hole is synchronous with the rotation of the male connector into the female connector.

13. The system of claim 12, wherein, there are four first connectors and four second connectors, and the through holes in the connection head and the through holes in the connection seat are arranged on a same circumference around respective center of end face, respectively.

14. The system of claim 10, wherein,
the limiting switch is arranged on a back side of the connection seat and includes a slider and a limiting plate, the slider is arranged in a slide extending along a movement direction of each second connector and is able to be moved along the slide between a locking position and a releasing position, a length of the slide is greater than a maximum travel of each second connector, and the limiting plate is fixedly connected with the slider; and
when the slider is positioned at the locking position, the limiting plate abuts against a rear end face of each second connector and limits each second connector in each through hole of the connection seat, and when the slider is positioned at the releasing position each second connector is able to be moved in a space in front of the limiting plate.

15. The system of claim 9, wherein,
the end face of the connection head is further provided with conductive contacts each of which is electrically connected with the camera unit, respectively;
the conductive interface is arranged on the end face of the connection seat; and
when the first connectors are engaged with the second connectors, the conductive contacts are electrically connected with the conductive interface.

* * * * *